United States Patent [19]

Haupt

[11] 4,007,497
[45] Feb. 15, 1977

[54] ARTIFICIAL FOOT WITH ANKLE JOINT

[75] Inventor: Werner Haupt, Duderstadt, Germany

[73] Assignee: Otto Boch Orthopadische Industries KG, Duderstadt, Germany

[22] Filed: Sept. 3, 1975

[21] Appl. No.: 609,995

[30] Foreign Application Priority Data

Sept. 5, 1974 Germany .................... 2442441

[52] U.S. Cl. ................................. 3/33; 3/7
[51] Int. Cl.² ................... A61F 1/04; A61F 1/08
[58] Field of Search ................... 3/30–35, 3/6, 7, 2

[56] References Cited

UNITED STATES PATENTS

| | | | |
|---|---|---|---|
| 2,594,945 | 4/1952 | Lucas et al. | 3/32 |
| 2,692,990 | 11/1954 | Schaefer | 3/32 |
| 2,731,645 | 1/1956 | Woodall | 3/6 |
| 2,923,948 | 2/1960 | Greissinger | 3/33 |
| 3,833,941 | 9/1974 | Wagner | 3/7 |

FOREIGN PATENTS OR APPLICATIONS 1,173,612 7/1964 Germany .................... 3/7

Primary Examiner—Ronald L. Frinks
Attorney, Agent, or Firm—Bosworth, Sessions & McCoy

[57] ABSTRACT

An artificial foot and ankle joint including a foot part having a plastic impregnated upper surface portion, an ankle part having a lower plastic impregnated articulation surface and a bifurcated joint connecting the two. The bifurcated joint has a lower part which contains an articulation axis and is connected into the foot part through the plastic impregnated surface portion of the foot part. The bifurcated joint also has an upper part generally U-shaped in cross-section which contacts the articulation axis from below. The upper part of the bifurcated joint is connected to the ankle part through the plastic impregnated recessed articulation surface of the ankle part. An elastic articulator is provided between the ankle part and the foot part and has a central opening for receiving the lower part of the bifurcated joint. The articulator has only a front dorsal projection and side rotation surfaces for cooperation with the plastic impregnated articulation surface of the ankle part. A separate exchangeable resilient member is provided between the ankle part and the foot part and behind the articulator for dorsal plantar flexion.

2 Claims, 3 Drawing Figures

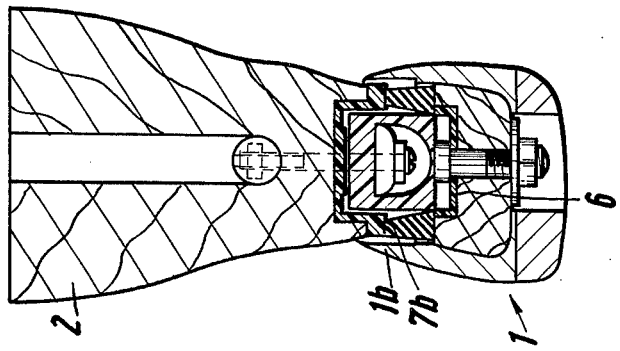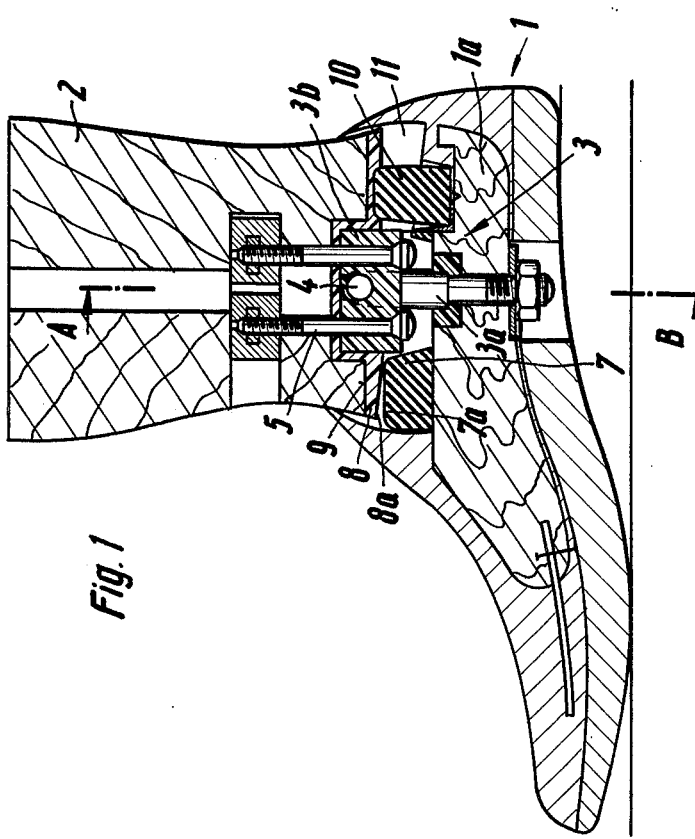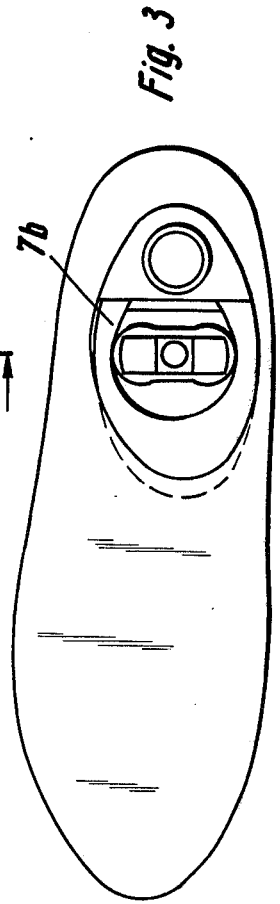

ARTIFICIAL FOOT WITH ANKLE JOINT

BACKGROUND OF THE INVENTION

This invention relates to an artificial foot and an ankle part connected by means of a two-part forked joint. The lower part of the latter which contains the articulation axis is screwed immovably into the foot part, separated by a plastic socket that is also firmly bonded to the foot part. The upper portion of the ankle joint which appears nearly U-shaped in a cross-sectional view and is made of a viscous, elastic material, grips the joint axis from below. It is immovably screwed into the ankle part, separated by a plastic socket that is also firmly bonded to the ankle.

In the socket of the foot part a ring-shaped articulator (which should be made of elastic material, preferably rubber) is loosely inserted to correspond to the dome-shaped articulation surface of the lower end of the ankle. The lower part of the ankle projects through the ring hole of the rubber articulator.

The present invention is an improvement of the previously known artificial foot joint disclosed in German Patent Specification No. 1,173,612. In the previous model the ring-shaped articulator, besides providing a rotation surface for the articulating surface of the ankle, also includes a dorsal projection in front and a rear projection for the plantar flexion. The disadvantage of this model lies in the absence of adaptability of the plantar flexion to the wearer of the prosthesis in regard to weight, age, etc.

In the previous model the sockets are discrete plastic molds that have been glued onto the corresponding surfaces of the wooden foot and ankle parts. This solution requires relatively complicated lathe work of the wooden parts as well as excessive space needs. The fastening of the plastic molds is difficult as they must be made of smooth, low friction material which is not suitable for gluing. Moreover, these molded plastic parts require excessive effort to place them in predetermined positions with sufficient precision.

Underneath the plastic socket of the foot part, the wood must have a sufficiently wide diameter to carry the transferred weight without failure. Because of the addition of the plastic part on top of this section of the wooden part, the articulation axis is relatively high. For an optimal approximation of natural conditions, however, it is in principle desirable to achieve the lowest possible position of the axis.

A further disadvantage is presented by the complicated production method required for the ball-shaped articulation surface of the wooden ankle. The lathe work for this surface must be extremely precise so that the plastic socket can be fitted tightly around it.

From a cosmetic point of view there is an additional disadvantage in that there is a visible gap in the joint between the foot and the ankle.

SUMMARY OF THE INVENTION

An object of the present invention is to improve the above-described artificial foot joint in such a way that it will make possible the adaptation of the plantar flexion to the wearer of the artificial limb and to ensure simplified construction methods.

The artificial foot and ankle joint embodying the present invention includes a foot part, an ankle part and a bifurcated joint connecting the two. The bifurcated joint includes a lower part which defines an articulation axis and is connected to said foot part and an upper elastic part connected to said ankle part and contacting said axis from below. An elastic articulator is provided between the foot part and the ankle part and extends along the front and sides of the foot part. A separate exchangeable, resilient member is provided between the ankle part and the foot part and behind the articulator for providing dorsal plantar flexion.

The invention fulfills the above objects in that the ring-shaped articulator presents only a dorsal projection in addition to the rotation surface for the articulation surface of the ankle, while a separate, exchangeable rubber knob is provided for dorsal plantar flexion.

By exchanging the separate rubber knob for a knob of a different degree of resiliency, it is possible in a simple manner to achieve the necessary adaptability to the individual requirements of the wearer.

In a working embodiment the two plastic sockets consist of molds that are sprayed onto the corresponding lathed surfaces of the wooden foot and ankle parts. The liquid plastic is sprayed directly on the relatively simply lathed surfaces of the wooden parts, thus creating an integrated wood and plastic construction. The wooden part thus forms half of the required molding tool. As the liquid plastic is introduced under high pressure, it flows into all pores, capillaries and similar openings of the wood, impregnating the wood and resulting in a tight fit between the two materials. This eliminates the tedious gluing job required in the previous model. Moreover, the plastic sockets can be produced very precisely in the desired location. As a result of the tight fitting bond between wood and plastic, the materials cannot slip out of place, thus eliminating all possible noise. The high pressure molding process causes the wood to be sealed and consequently strengthened. To prevent the splitting of the wood during the high pressure process, the use of a washer is recommended which provides a tight ring around the relevant surface and can be pressed tightly into the wood. This will achieve stabilization of the wooden part.

The integrated wood and plastic piece makes possible a narrower diameter of the part, thus enabling the articulating axis to be positioned much lower than is possible in the previous model.

In contrast to the previous model, the upper plastic socket forms the lower end of the ankle and thus of its ball-shaped articulating surface. This construction provides a great production advantage in that the plastic part can be sprayed on a plane ankle surface even before the machining of the outside of the ankle. The machining of the ankle surface simultaneously shapes the sprayed-on plastic in corresponding outer contours. This completely eliminates the lathe work for a ball-shaped wooden surface and the separate production of plastic molds.

A working embodiment will preferably include a cosmetic cover of specific design which camouflages the gap in the joint. This also makes it possible inside the foot part to shift the sprayed-on plastic part in the direction of the toes so that for the first time this joint construction is now also suitable for smaller shoe sizes.

BRIEF DESCRIPTION OF THE DRAWINGS

FIG. 1 is a side view of an artificial foot with ankle joint embodying the present invention.

FIG. 2 is a cross-sectional view along the line A-B in FIG. 1.

FIG. 3 is a top view of the foot part of the present invention.

DESCRIPTION OF A PREFERRED EMBODIMENT

Referring now to the drawings, the artificial foot and ankle joint includes foot part 1, ankle part 2 and a connecting bifurcated joint 3. The upper joint part 3b consisting of viscous elastic plastic and being almost U-shaped in cross-section, grips foot and ankle joint axis 4 from below and is immovably screwed to ankle part 2 by means of bolts 5.

The lower joint part 3a fastens a plastic socket 6 against the wooden part 1a of the foot 1. This plastic socket 6 is sprayed directly onto the corresponding lathed surface of the wood piece 1a, thus forming an integrated construction (FIG. 1).

In wooden part 1a of foot 1 a ring-shaped rubber articulator 7 is loosely inserted. Its side facing the toes forms the dorsal projection 7a and its lateral parts from the rotation surfaces 7b. The latter correspond to the dome-shaped articulation surface 8a of a plastic socket 8 which is sprayed directly on the lower plane end 9 of ankle part 2, and which serves as support for upper joint part 3b as well as a rotation plane for articulator 7 and as support for rubber knob 10.

The latter is inserted as an exchangeable part behind articulator 7 and acts as dorsally located plantar flexion. Foot part 1 is covered with cosmetic cover 1b which camouflages the gap in the joint 11.

What is claimed is:

1. An artificial foot and ankle joint, comprising a foot part having an upper surface including a plastic impregnated socket, an ankle part having a plastic impregnated lower surface including a centrally located plastic impregnated socket and surrounding plastic impregnated articulation surfaces, and a bifurcated joint connecting said foot part and ankle part, said bifurcated joint having a lower part which contains an articulation axis and is connected immovably into said foot part through said plastic impregnated socket of said foot part, said bifurcated joint having an upper part made of elastic material and generally U-shaped in cross-section which contacts said axis from below, said upper part being connected to said ankle part through said plastic impregnated socket of said ankle part, an elastic articulator between said ankle part and said foot part contacting said plastic impregnated articulation surface of the ankle part, said articulator having a central opening for receiving said lower part of said bifurcated joint, said articulator having only a front dorsal projection and side rotation surfaces for cooperation with said plastic impregnated articulation surfaces of said ankle part, and a separate, exchangeable resilient member between said ankle part and said foot part and behind said articulator for dorsal plantar flexion, said resilient member contacting said plastic impregnated articulation surface of said ankle part.

2. An artificial foot and ankle joint as claimed in claim 1 wherein a cosmetic cover is provided to cover gaps between said foot and ankle parts.

* * * * *

UNITED STATES PATENT AND TRADEMARK OFFICE
CERTIFICATE OF CORRECTION

PATENT NO. : 4,007,497
DATED : February 15, 1977
INVENTOR(S) : Werner Haupt

It is certified that error appears in the above–identified patent and that said Letters Patent are hereby corrected as shown below:

Correct name of Assignee to read as follows:

OTTO BOCK ORTHOPADISCHE INDUSTRIE KG

Signed and Sealed this

Third Day of May 1977

[SEAL]

Attest:

RUTH C. MASON
*Attesting Officer*

C. MARSHALL DANN
*Commissioner of Patents and Trademarks*